US006294087B1

(12) United States Patent
Hargro et al.

(10) Patent No.: US 6,294,087 B1
(45) Date of Patent: *Sep. 25, 2001

(54) CHROMATOGRAPHY COLUMN

(75) Inventors: Ivan Hargro; Jeffrey A. Horsman, both of Charlottesville; Peter C. Rahn, Palmyra; Peter C. Van Davelaar, Maidens, all of VA (US)

(73) Assignee: Dyax Corporation, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/548,261

(22) Filed: Apr. 12, 2000

Related U.S. Application Data

(62) Division of application No. 09/137,278, filed on Aug. 20, 1998, now Pat. No. 6,139,733.

(51) Int. Cl.⁷ .................................................. B01D 15/08
(52) U.S. Cl. .......................... 210/198.2; 210/656; 96/101
(58) Field of Search ..................................... 210/635, 656, 210/659, 198.2, 232, 238, 282; 96/101, 105, 106

(56) References Cited

U.S. PATENT DOCUMENTS

| | | | |
|---|---|---|---|
| 3,266,554 | 8/1966 | Brownrigg | 210/198.2 |
| 3,398,512 | 8/1968 | Perkins, Jr. et al. | 55/386 |
| 3,615,235 | 10/1971 | Hrdina | 210/198.2 |
| 3,682,315 * | 8/1972 | Haller | 210/198.2 |
| 3,692,669 | 9/1972 | Bauman | 210/198.2 |
| 3,763,879 | 10/1973 | Jaworek | 137/268 |
| 3,902,849 | 9/1975 | Barak et al. | 210/198.2 |
| 4,093,550 * | 6/1978 | Stahl | 210/198.2 |
| 4,250,035 | 2/1981 | McDonald et al. | 210/198.2 |
| 4,457,846 | 7/1984 | Munk | 210/198.2 |
| 4,483,374 | 11/1984 | Siemion | 141/9 |
| 4,565,532 | 1/1986 | Hatch et al. | 210/656 |
| 4,636,316 | 1/1987 | Harris et al. | 210/656 |
| 4,719,011 | 1/1988 | Shalon et al. | 210/198.2 |
| 4,732,687 | 3/1988 | Muller et al. | 210/656 |
| 4,876,005 | 10/1989 | America | 210/198.2 |
| 4,968,421 | 11/1990 | Spacek et al. | 210/198.2 |
| 5,227,059 | 7/1993 | Shepherd | 210/198.2 |
| 5,324,427 | 6/1994 | Traveset-Masanes et al. | 210/198.2 |
| 5,338,448 | 8/1984 | Gjerde | 210/198.2 |
| 5,462,660 | 10/1995 | Singleton | 210/198.2 |
| 5,601,708 | 2/1997 | Leavesley | 210/198.2 |
| 5,614,089 | 3/1997 | Allington | 210/198.2 |

OTHER PUBLICATIONS

Larry Miller, et al., "Solid injection, a new technique for application of insoluble samples in preparative liquid chromatography," Journal of Chromatography, vol. 484 (1989), pp. 259–265.

J. Kriz et al., "Solid sample introduction in preparative high–performance liquid chromatography: separation of diamantanols," Journal of Chromatography, vol. 248 (1982), pp. 303–307.

Patrick D. McDonald et al., "Strategies for successful preparative liquid chromatography," Chapter 1, section 1.6.2.2.6, "Sample Solubility," pp. 79–80, in Brian A. Bidlingmeyer, ed., Preparative Liquid Chromatography, (Amsterdam: Elsevier, 1987).

"Flash Sample Injection Module ™," Biotage, a Division of Dyax Corp., (1996), pp. 1 and 2.

Snyder, "Introduction to Modern Liquid Chromatography," (New York: John Wiley & Sons, 1979), pp. 228–229, 251, 543, and 635.

* cited by examiner

Primary Examiner—Ernest G. Therkorn
(74) Attorney, Agent, or Firm—Fish & Richardson P.C.

(57) ABSTRACT

A chromatography column includes a tubular member with an inlet end and a slidable porous member that bounds a chromatography media. The porous member is spaced sufficiently from the inlet end to define a receiving region.

18 Claims, 3 Drawing Sheets

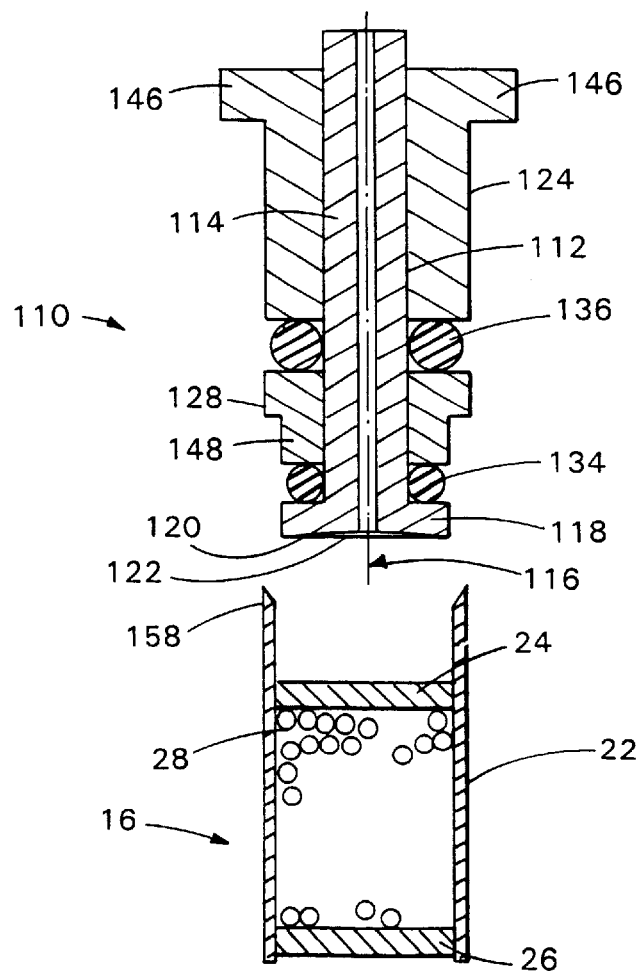
FIG. 5
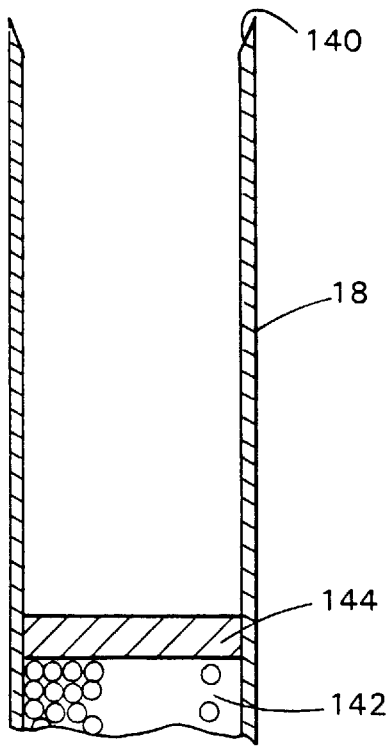

CHROMATOGRAPHY COLUMN

REFERENCE TO RELATED APPLICATIONS

This application is a division of U.S. patent application Ser. No. 09/137,278, filed Aug. 20, 1998, now U.S. Pat. No. 6,139,733, the entire contents of which are hereby incorporated by reference.

BACKGROUND OF THE INVENTION

The invention relates to introducing a sample into a chromatography column.

Liquid chromatography is a technique for separating the individual compounds that exist in a subject sample. In employing the technique, the subject sample is carried in a liquid, called a mobile phase. The mobile phase carrying the subject sample is caused to migrate through a media, called a stationary phase. Different compounds will have differing rates of migration through the media, which effects the separation of the components in the subject sample. Liquid chromatography is commonly performed with reusable columns or with disposable cartridges, both of which are usually cylindrical, in which the media bed is bounded axially by porous plates, or plates containing defined flow paths, through which the mobile phase will flow. (See U.S. Pat. No. 4,250,035 to McDonald et al. and U.S. Pat. No. 5,601,708 to Leavesley)

When chemists optimize liquid chromatographic separations conditions, they may need to dissolve the sample mixture in a dissolution solvent which may be nonideal for elution. This can result in poor separation and poor recovery of desired components.

One solution to this problem is to pre-absorb the sample onto a media prior to chromatography. This involves dissolving the sample mixture in a suitable solvent and adding an amount of a dry media (usually similar to the media being used for the separation) to this solution. The dissolution solvent is then evaporated off, usually using a rotary evaporator, leaving the sample mixture dry, and absorbed to the media. The pre-absorbed media is then placed at the head of a pre-packed glass, metal or plastic chromatography column, and the optimized chromatographic solvent would flow through the pre-absorbed media and then through the column of separation media. This method has the potential hazard of the operator coming into contact with the dry powdery media both before and after the addition of the sample. This method also can lead to poor separations and recovery.

SUMMARY OF THE INVENTION

In one aspect, the invention features, in general, a chromatography sample module including a flow-through member having an inlet and an outlet and chromatography media within the flow-through member. A sample is added to the media, and the module, with the sample carried therein, can then be connected to a separation column.

Preferably the chromatography sample module is a tubular member that is sized to fit within the end of a chromatography column that is used for separation of the sample contained on the media in the module. Alternatively, the module can be connected to the chromatography separation column by a flow line. The sample in the dissolution solvent can be added to the sample module, and then the dissolution solvent can be evaporated. Alternatively, the sample in the dissolution solvent can be added to the sample module as a liquid without evaporation.

In another aspect the invention features a rack of sample modules arranged in an array.

Embodiments of the invention may include one or more of the following advantages. The samples can be easily introduced into separation columns. Various solvents can be used for separation and dissolution of the sample, permitting optimization of the separation procedure. Samples are easily preprocessed, and the operator is not exposed to the media before or after adding the sample. A large number of samples can be prepared for processing at one time, facilitating the carrying out of multiple separations at one time.

Other features and advantages of the invention will be apparent from the following description of the preferred embodiments thereof and from the claims.

BRIEF DESCRIPTION OF THE DRAWINGS

FIG. 5 is a vertical sectional view showing the FIG. 2 sample module in position between a sealing head and a chromatography column used in the FIG. 1 system prior to assembly.

DESCRIPTION OF THE PREFERRED EMBODIMENTS

Figure 1:
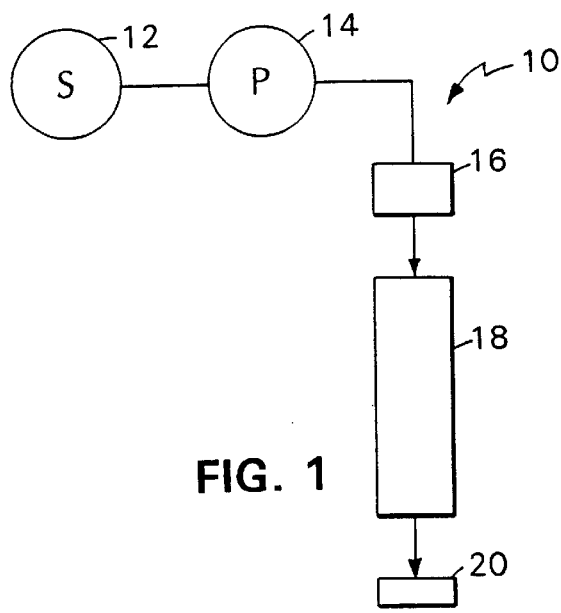
FIG. 1 is a schematic diagram of a chromatography system according to the invention.

Referring to FIG. 1, there is shown chromatography system 10 which includes a source of solvent 12, pump 14, sample module 16, liquid chromatography column 18, and sample collection vessel 20. In this system, the sample to be analyzed is preabsorbed onto media in sample module 16 prior to pumping solvent into module 16 and into chromatography column 18 to perform the separation procedure.

Figure 2:
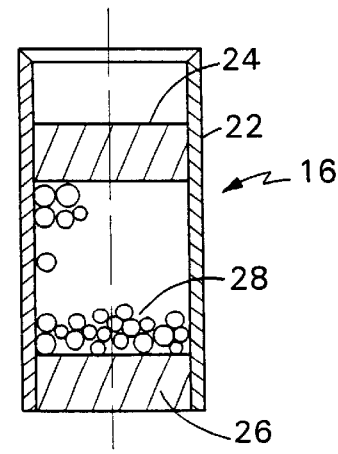
FIG. 2 is a vertical sectional view of a chromatography sample module used in the FIG. 1 system.

Referring to FIG. 2, it is seen that sample module 16 includes cylindrical plastic tube 22, porous plates 24, 26 (made of inert plastic porous frits), and chromatography media 28 (only partially shown in the figures) between porous plates 24, 26.

Figure 6:
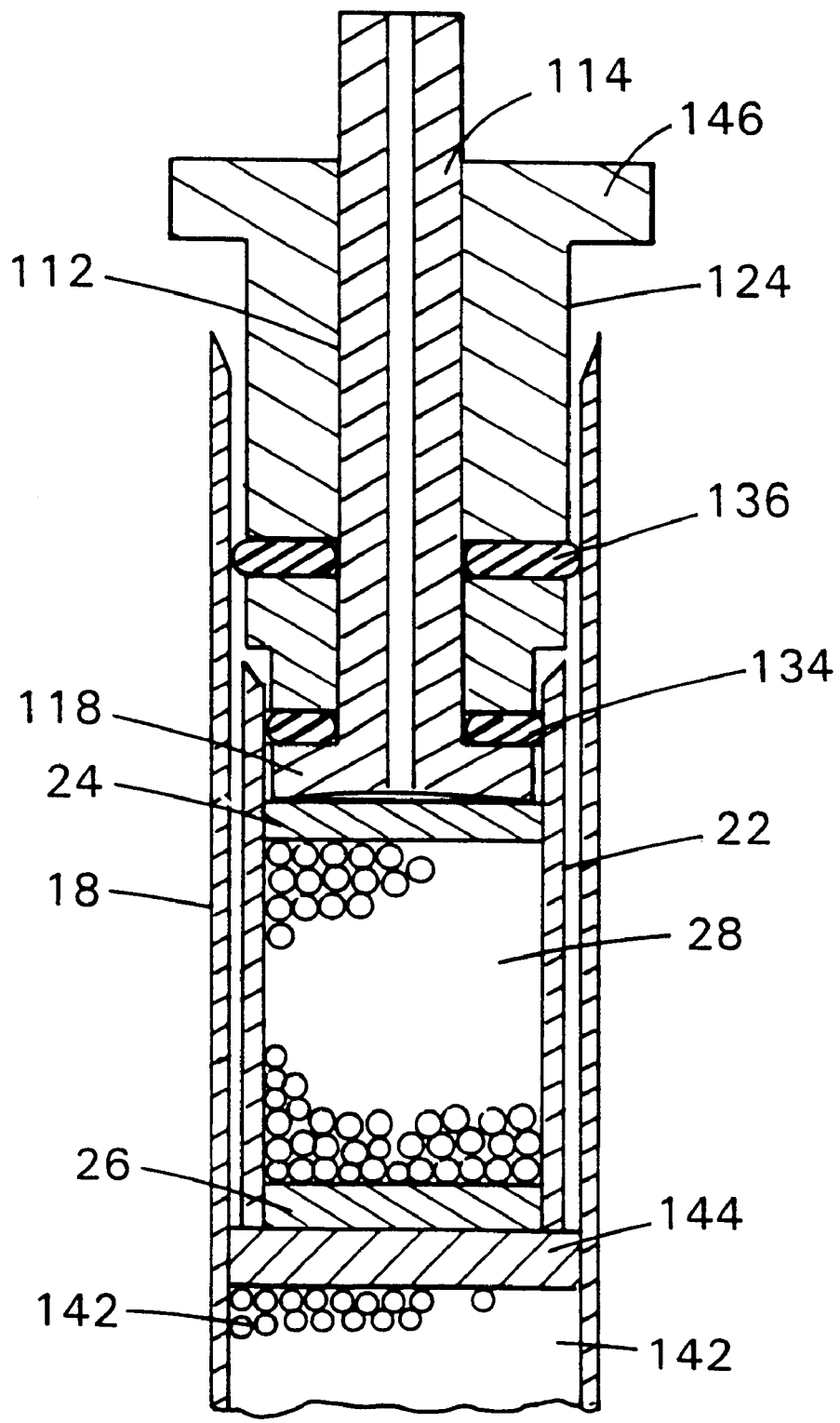
FIG. 6 is a vertical sectional view showing the FIG. 5 components in an assembled and sealed state.

As appears from FIGS. 5 and 6, sample module 16 is designed to fit within chromatography column 18 at the entrance thereof and to be sealably connected to the sealing head. Tube 22 is designed to fit within column 18 with minimal space between the two; in particular, there is 0.000" to 0.010" of radial clearance.

Sample module 16 can be filled with media that is the same as or is different from the media of chromatography column 18. The sample is dissolved in the required solvent and added to the top of sample module 16, where it is drawn into the media by capillary action. This dissolution solvent is then removed by placing sample module 16 in a vacuum chamber. Heat may also be applied.

After sample module 16 has dried, it can be placed directly inside separation column 18 so that the lower porous plate 26 is an in intimate contact with the surface of the separation media or with a porous plate within the separation column on top of the separation media.

Alternatively, sample module 16 can be placed in a remote tube connected by a solvent line. Alternatively, the sample can be dissolved in a separation solvent or a weaker solvent), and added to module 16. The wet module can then be loaded into the column or into a remote tube.

Examples of the types of complex samples where this technique has particularly advantageous use include synthetic organic reaction mixtures and natural product extracts, (e.g., from fermentation broths or plants). These samples often need to be dissolved in a solvent not compatible with the optimized separation solvent. Solvents are organized according to their "solvent strength," where hexanes have a value close to zero, and methanol has a value of 0.95. Optimized separation eluents often have a lower solvent strength; e.g., hexane:ethylacetate 1:1 has a solvent strength of 0.295. If the sample needs to be dissolved in a strong solvent such as methanol, there will be a solvent strength difference of 0.655 seen initially after loading the sample onto the column, and this will impair the separation of the sample. If the sample dissolved in methanol is instead preadsorbed to the media in the sample module and dried, the sample will not face this impairment during separation.

Figure 3:
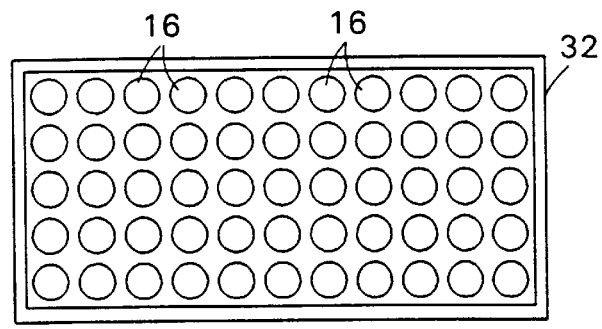
FIG. 3 is a plan view of a rack containing a plurality of the FIG. 2 sample modules in an array.
Figure 4:
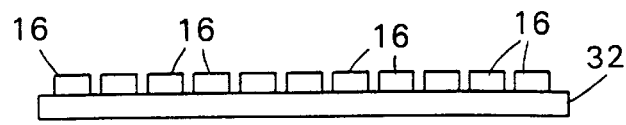
FIG. 4 is an elevation of the FIG. 3 rack and modules.

Referring to FIGS. 3 and 4, sample modules 16 can be supplied in racks 32, and a whole rack of sample modules 16 can be efficiently prepared at one time rather than one at a time.

FIGS. 5 and 6 show the placement of a module 16 in a column 18 and the sealing of the module 16 and column 18 to a sealing head used to deliver solvent. Sealing head 110 has first head piece 112, second head piece 124, intermediate head piece 128, and first and second annular elastomeric sealing members 134, 136.

First head piece 112 has body 114 with longitudinal axis 116. First head piece 112 has outwardly extending shoulder 118, and contact face 120. Part of contact face 120 has a slightly conical shape or other concavity. First head piece 112 defines flow path 122 along axis 116.

Body 114 of first head piece 112 fits slidably through central openings in second head piece 124, intermediate head piece 128, and first and second elastomeric sealing members 134, 136.

Second head piece 124 has outwardly extending compression member 146. Intermediate head piece 128 has narrow portion 148 distal from second head piece 124.

First elastomeric sealing member 134 is adjacent to both shoulder 118 and narrow portion 148 of intermediate head piece 128. Second elastomeric sealing member 136 is adjacent to both intermediate head piece 128 and second head piece 124.

The outer diameter of tube 22 of sample module 16 is sized so that tube 22 fits into column 18. The inner diameter of tube 22 is sized so that it may slidably receive shoulder 118, first elastomeric sealing member 134, and narrow portion 148 of intermediate head piece 128.

Intermediate head piece 128, second elastomeric sealing member 136, and second head piece 124 are sized to fit slidably into column 18, having chamfered edges 140, filled with chromatography separation media 142, which is bounded axially by porous plates 144.

Referring to FIG. 6 seals are formed with the apparatus by inserting sample module 16 into column 18 so that second porous plate 26 abuts first porous plate 144. Referring to FIG. 5, sealing head 110 is then inserted into column 18 and tube 22 of sample module 16, so that shoulder 118, first elastomeric sealing member 134, and narrow portion 148 are within tube 22, and contact face 120 abuts porous plate 24. Sealing head 110 extends far enough into column 18 so that second elastomeric sealing member 136 opposes the inner surface of column 18.

Downward compressive force applied to outwardly extending compression member 146 causes second head piece 124 to slide relative to first head piece 112 and transmits compressive force to second elastomeric sealing member 136, intermediate head piece 128, first elastomeric sealing member 134, shoulder 118, porous plate 24, sample module media 28, porous plate 26, porous plate 144, and separation media bed 142. The compressive force causes first and second elastomeric sealing members 134, 136 to expand radially so that first elastomeric sealing member 134 forms a seal with tube 22, and second elastomeric sealing member 136 forms a seal with column 18.

The seals are released by relaxing or removing the downward force to second head piece 124, thereby reducing the compressive force on the components of sealing head 110 and reducing the radial expansion of elastomeric sealing members 134, 136.

Preferably, tube 22 and column 18 are made of high-density polyethylene. However, the columns may be constructed of other materials, including glass or stainless steel. Preferably, elastomeric sealing members are made of a fluorocarbon polymer, such as that sold under the trade name CHEMRAZ.

Other embodiments of the invention are within the scope of the following claims.

What is claimed is:

1. A chromatography column for accepting a sample module comprising:
   a tubular member having an inlet end, an outlet end, and an inner surface;
   first and second porous members disposed within said tubular member; and
   a chromatography media disposed within said tubular member and bounded by said first and second porous members;
   wherein said first porous member abuts said chromatography media and said first porous member is also in downwardly slidable contact with said inner surface of said tubular member and is spaced sufficiently from said inlet end to define a module receiving region for receiving a sample module entirely within said tubular member.

2. The chromatography column of claim 1, wherein said tubular member further comprises a sealing region between said inlet end and said module receiving region, said sealing region being sufficiently long to receive a sealing head for making a seal with said inner surface of said tubular member.

3. The chromatography column of claim 1 wherein said inner surface of said tubular member is substantially cylindrical throughout said module receiving region.

4. The chromatography column of claim 1 wherein said tubular member comprises polyethylene.

5. The chromatography column of claim 1 wherein said tubular member comprises stainless steel.

6. The chromatography column of claim 1 wherein said tubular member comprises glass.

7. A chromatography column for use with a sample module comprising:
   a tubular member having an inlet end, an inner surface, and a module receiving region, said module receiving region being bounded by said inlet end and by a porous member;
   a chromatography media inside said tubular member, said chromatography media being bounded by said porous member;

wherein said porous member abuts said chromatography media and said first porous member is also in downwardly slidable contact with said inner surface of said tubular member and is spaced sufficiently from said inlet end so that said module receiving region is deep enough to permit a sample module to be inserted completely into said receiving region.

8. The chromatography column of claim 7, wherein said tubular member further comprises a sealing region between said inlet end and said module receiving region, said sealing region being sufficiently long to receive a sealing head for making a seal with said inner surface of said tubular member.

9. The chromatography column of claim 7 wherein said inner surface of said tubular member is substantially cylindrical throughout said module receiving region.

10. The chromatography column of claim 7 wherein said tubular member comprises polyethylene.

11. The chromatography column of claim 7 wherein said tubular member comprises stainless steel.

12. The chromatography column of claim 7 wherein said tubular member comprises glass.

13. A chromatography column for accepting a sample module comprising:

a tubular member having an inlet end, an outlet end, and an inner surface said tubular member having a chamfered region near said inlet end;

first and second porous members disposed within said tubular member; and a chromatography media disposed within said tubular member and between said first and second porous members;

wherein said first porous member is slidably fitted within said tubular member and is spaced sufficiently from said inlet end to define a module receiving region for receiving a sample module entirely within said tubular member.

14. The chromatography column of claim 13, wherein said tubular member further comprises a sealing region between said inlet end and said module receiving region, said sealing region being sufficiently long to receive a sealing head for making a seal with said inner surface of said tubular member.

15. The chromatography column of claim 14 wherein said inner surface of said tubular member is substantially cylindrical throughout said module receiving region.

16. The chromatography column of claim 13 wherein said tubular member comprises polyethylene.

17. The chromatography column of claim 13 wherein said tubular member comprises stainless steel.

18. The chromatography column of claim 13 wherein said tubular member comprises glass.

* * * * *

(12) EX PARTE REEXAMINATION CERTIFICATE (7112th)
United States Patent
Hargro et al.

(10) Number: US 6,294,087 C1
(45) Certificate Issued: Oct. 20, 2009

(54) CHROMATOGRAPHY COLUMN

(75) Inventors: Ivan Hargro, Charlottesville, VA (US); Jeffrey A. Horsman, Charlottesville, VA (US); Peter C. Rahn, Palmyra, VA (US); Peter C. Van Davelaar, Maidens, VA (US)

(73) Assignee: Biotage, Inc., Charlottesville, VA (US)

Reexamination Request:
No. 90/008,969, Feb. 6, 2008

Reexamination Certificate for:
Patent No.: 6,294,087
Issued: Sep. 25, 2001
Appl. No.: 09/548,261
Filed: Apr. 12, 2000

Related U.S. Application Data

(62) Division of application No. 09/137,278, filed on Aug. 20, 1998, now Pat. No. 6,139,733.

(51) Int. Cl.
*B01D 15/08* (2006.01)
*G01N 30/52* (2006.01)
*G01N 30/00* (2006.01)
*G01N 30/16* (2006.01)
*G01N 30/08* (2006.01)
*G01N 30/60* (2006.01)

(52) U.S. Cl. ........................ 210/198.2; 210/656; 96/101
(58) Field of Classification Search ........................ None
See application file for complete search history.

(56) References Cited

U.S. PATENT DOCUMENTS

| | | | |
|---|---|---|---|
| 3,463,320 | A | 8/1969 | Patterson |
| 4,769,141 | A | 9/1988 | Couillard |
| 5,863,428 | A | 1/1999 | Ma et al. |
| 6,177,008 | B1 | 1/2001 | Treiber et al. |

FOREIGN PATENT DOCUMENTS

JP     53-015197     2/1978

OTHER PUBLICATIONS

Liquid Chromatography Columns. [online]. Department of Chemistry, The University of Adelaide (Australia) [retrieved on Mar. 30, 2009]. Retrieved from the Internet: <URL: www.chemistry.adelaide.edu.au/external/soc-rel/content/lc-col.htm>.*

English language translaton of an Office Action issued Feb. 10, 2009 by the Japanese Patent Office in Japanese Patent Application No. 2000-565989.

International Sorbent Technology Catalogue, 1993.

* cited by examiner

*Primary Examiner*—Dwayne C Jones

(57) ABSTRACT

A chromatography column includes a tubular member with an inlet end and a slidable porous member that bounds a chromatography media. The porous member is spaced sufficiently from the inlet end to define a receiving region.

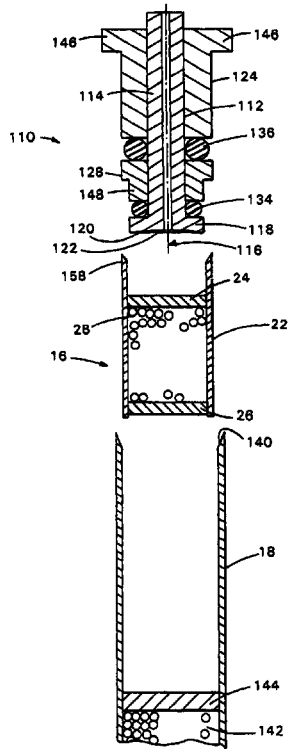

US 6,294,087 C1

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 2, lines 35–41:

Referring to FIG. 1, there is shown chromatography system 10 which includes a source of solvent 12, pump 14, sample module 16, liquid chromatography column 18, and sample collection vessel 20. In this system, the sample to be analyzed is preabsorbed onto a *a sample module chromatography* media 28 in sample module 16 prior to pumping solvent into module 16 and into chromatography column 18 to perform the separation procedure.

Column 2, lines 42–46:

Referring to FIG. 2, it is seen that sample module 16 includes cylindrical plastic tube 22, porous plates 24, 26 (made of inert plastic porous frits), and *sample module* chromatography media 28 (only partially shown in the figures) between porous plates 24, 26.

Column 2, lines 53–59:

Sample module 16 can be filled with *a sample chromatography* media that is the same as or is different from the *chromatography separation* media of chromatography column 18. The sample is dissolved in the required solvent and added to the top of sample module 16, where it is drawn into the media by capillary action. This dissolution solvent is then removed by placing a sample module 16 in a vacuum chamber. Heat may also be applied.

Column 2, lines 60–64:

After sample module 16 has dried, it can be placed directly inside separation column 18 so that the lower porous plate 26 is an in intimate contact with the surface of the *chromatography* 142 separation media or with a porous plate within the separation column on top of the *chromatography* separation media *142*.

Column 3, lines 4–20:

Examples of the types of complex samples where this technique has particularly advantageous use include synthetic organic reaction mixtures and natural product extracts, (e.g., from fermentation broths or plants). These samples often need to be dissolved in a solvent not compatible with the optimized separation solvent. Solvents are organized according to their "solvent strength," where hexanes have a value close to zero, and methanol has a value of 0.95. Optimized separation eluents often have a lower solvent strength; e.g., hexane:ethylacetate 1:1 has a solvent strength of 0.295. If the sample needs to be dissolved in a strong solvent such as methanol, there will be a solvent strength difference of 0.655 seen initially after loading the sample onto the column, and this will impair the separation of the sample. If the sample dissolved in methanol is instead preadsorbed to the *sample chromatography* media in the sample module and dried, the sample will not face this impairment during separation.

Column 4, lines 3–14:

Downward compressive force applied to outwardly extending compression member 146 causes second head piece 124 to slide relative to first head piece 112 and transmits compressive force to second elastomeric sealing member 136, intermediate head piece 128, first elastomeric sealing member 134, shoulder 118, porous plate 24, sample module *chromatography* media 28, porous plate 26, porous plate 144, and *the bed of* separation *chromatography* media [bed]142. The compressive force causes first and second elastomeric sealing members 134, 136 to expand radially so that first elastomeric sealing member 134 forms a seal with tube 22, and second elastomeric sealing member 136 forms a seal with column 18.

AS A RESULT OF REEXAMINATION, IT HAD BEEN DETERMINED THAT:

Claims 1–18 are determined to be patentable as amended.

1. A chromatography *set having a chromatography* column [for accepting] *and* a sample module, comprising:
   *the chromatography column having*
      a tubular member having an inlet end, and outlet end, and an inner surface;
      first and second porous members disposed within said tubular member; and
      a chromatography *separation* media disposed within said tubular member and bounded by said first and second porous members;
      wherein said first porous member abuts said chromatography *separation* media and said first porous member is also in downwardly slidable contact with said inner surface of said tubular member and is spaced sufficiently from said inlet end to define a module receiving region for receiving a sample module entirely within said tubular member; *and*
   *the sample module having*
      *a tubular flow-through member having an inlet and an outlet; and*
      *a sample module chromatography media disposed within said tubular flow-through member.*

2. The chromatography [column] *set* of claim 1, wherein said tubular member further comprises a sealing region between said inlet end and said module receiving region, said sealing region being sufficiently long to receive a sealing head for making a seal with said inner surface of said tubular member.

3. The chromatography [column] *set* of claim 1 wherein said inner surface of said tubular member is substantially cylindrical throughout said module receiving region.

4. The chromatography [column] *set* of claim 1 wherein said tubular member comprises polyethylene.

5. The chromatography [column] *set* of claim 1 wherein said tubular member comprises stainless steel.

6. The chromatography [column] *set* of claim 1 wherein said tubular member comprises glass.

7. A chromatography *set including a chromatography* column *and* for use with a sample module, comprising:
   *the chromatography column having*
      a tubular member having an inlet end, an inner surface, and a module receiving region, said module receiving region being bounded by said inlet end and by a porous member;
      a chromatography *separation* media inside said tubular member, said chromatography *separation* media being bounded by said porous member;

wherein said porous member abuts said chromatography *separation* media and said first porous member is also in downwardly slideable contact with said inner surface of said tubular member and is spaced sufficiently from said inlet end so that said module receiving region is deep enough to permit a sample module to be inserted completely into said receiving region; *and*

*the sample module having*

*a tubular flow-through member having an inlet and an outlet; and*

*a sample module chromatography media disposed within said tubular flow-through member.*

8. The chromatography [column] *set* of claim 7, wherein said tubular member further comprises a sealing region between said inlet end and said module receiving region, said sealing region being sufficiently long to receive a sealing head for making a seal with said inner surface of said tubular member.

9. The chromatography [column] *set* of claim 7 wherein said inner surface of said tubular member is substantially cylindrical throughout said module receiving region.

10. The chromatography [column] *set* of claim 7 wherein said tubular member comprises polyethylene.

11. The chromatography [column] *set* of claim 7 wherein said tubular member comprises stainless steel.

12. The chromatography [column] *set* of claim 7 wherein said tubular member comprises glass.

13. A chromatography *set including a chromatography* column for accepting a sample module, comprising:

a tubular member having an inlet end, an outlet end, and an inner surface said tubular member having a chamfered region near said inlet end;

first and second porous members disposed within said tubular member; and a chromatography *separation* media disposed within said tubular member and between said first and second porous members;

wherein said first porous member is slidably fitted within said tubular member and is spaced sufficiently from said inlet end to define a module receiving region for receiving a sample module entirely within said tubular member; *and*

*the sample module having*

*a tubular flow-through member having an inlet and an outlet; and*

*a sample module chromatography media disposed within said tubular flow-through member.*

14. The chromatography [column] *set* of claim 13, wherein said tubular member further comprises a sealing region between said inlet end and said module receiving region, said sealing region being sufficiently long to receive a sealing head for making a seal with said inner surface of said tubular member.

15. The chromatography [column] *set* of claim 14 wherein said inner surface of said tubular member is substantially cylindrical throughout said module receiving region.

16. The chromatography [column] *set* of claim 13 wherein said tubular member comprises polyethylene.

17. The chromatography [column] *set* of claim 13 wherein said tubular member comprises stainless steel.

18. The chromatography [column] *set* of claim 13 wherein said tubular member comprises glass.

\* \* \* \* \*